(12) United States Patent
Dooney, Jr.

(10) Patent No.: US 10,888,311 B2
(45) Date of Patent: Jan. 12, 2021

(54) SUTURE ANCHOR WITH BIOLOGIC PROXIMAL END

(71) Applicant: Arthrex, Inc., Naples, FL (US)

(72) Inventor: Thomas Dooney, Jr., Naples, FL (US)

(73) Assignee: Arthrex, Inc., Naples, FL (US)

( * ) Notice: Subject to any disclaimer, the term of this patent is extended or adjusted under 35 U.S.C. 154(b) by 243 days.

(21) Appl. No.: 16/138,172

(22) Filed: Sep. 21, 2018

(65) Prior Publication Data

US 2020/0093476 A1    Mar. 26, 2020

(51) Int. Cl.
*A61B 17/04* (2006.01)
*A61B 17/00* (2006.01)

(52) U.S. Cl.
CPC ........ *A61B 17/0401* (2013.01); *A61B 2017/00004* (2013.01); *A61B 2017/00964* (2013.01); *A61B 2017/044* (2013.01); *A61B 2017/0409* (2013.01); *A61B 2017/0445* (2013.01); *A61B 2017/0458* (2013.01); *A61B 2017/0464* (2013.01)

(58) Field of Classification Search
CPC ...... A61B 17/0401; A61B 2017/00004; A61B 2017/00933; A61B 2017/00964; A61B 2017/0409; A61B 2017/044; A61B 2017/0445; A61B 2017/0458; A61B 2017/0464; A61L 31/005; A61L 31/148; Y10S 606/909
See application file for complete search history.

(56) References Cited

U.S. PATENT DOCUMENTS

| | | | |
|---|---|---|---|
| 5,061,286 A * | 10/1991 | Lyle | A61L 27/3608 623/23.63 |
| 5,868,749 A | 2/1999 | Reed | |
| 6,508,830 B2 | 1/2003 | Steiner | |
| 6,517,542 B1 | 2/2003 | Papay et al. | |
| 6,685,728 B2 | 2/2004 | Sinnott et al. | |
| 8,702,754 B2 | 4/2014 | DiMatteo et al. | |
| 8,961,561 B2 | 2/2015 | Schulman | |
| 9,700,297 B2 | 7/2017 | Schmieding | |
| 2003/0065332 A1* | 4/2003 | Tenhuisen | A61F 2/0811 606/312 |
| 2006/0229671 A1 | 10/2006 | Steiner et al. | |
| 2006/0247642 A1 | 11/2006 | Stone et al. | |

FOREIGN PATENT DOCUMENTS

WO    WO 02/087413 A2    11/2002

* cited by examiner

*Primary Examiner* — Kathleen S Holwerda
*Assistant Examiner* — Brooke Labranche
(74) *Attorney, Agent, or Firm* — Blank Rome LLP

(57) ABSTRACT

A suture anchor for tissue repair that has a proximal section and a main section where the proximal and main sections are formed of different materials. Only the proximal section is formed of a biologic material, such as human cortical bone. The proximal section is about one-third of the body of the anchor.

17 Claims, 3 Drawing Sheets

SUTURE ANCHOR WITH BIOLOGIC PROXIMAL END

FIELD OF THE INVENTION

The present invention relates to a suture anchor for anchoring sutures into bone.

BACKGROUND OF THE INVENTION

When soft tissue tears away from bone, reattachment becomes necessary. Various devices, including sutures alone, screws, staples, wedges, and plugs have been used in the to secure soft tissue to bone. Various types of threaded suture anchors have been developed for this purpose. However, a need exists for a suture anchor that has improved engagement and pull-out strength when installed in a bone hole.

SUMMARY OF THE INVENTION

Accordingly, the present invention provides a suture anchor for tissue repair with a cannulated anchor body that has proximal and distal ends, and an insertion length therebetween. The cannulated anchor body includes a proximal section and a main section. The proximal section is remote from the distal end and ends at the proximal end of the cannulated anchor body and the main section ends at the distal end of the cannulated anchor body. The proximal and main sections are formed of different materials. Preferably, the proximal section is formed of a biologic material, such as human cortical bone.

In some embodiments, the proximal section is no more than about one-third of the insertion length of the cannulated anchor body; the main section is formed of a biocompatible material, such as a bioabsorbable material, a biocomposite composite material, PLLA or nonabsorbable PEEK; the main section includes an inwardly tapered portion near the distal end; the cannulated anchor body has outwardly extending threads; and/or the cannulated anchor body includes an inner bore adapted to receive an inserter.

The proximal end is preferably configured to interface with an inserter, and the distal end is configured to cooperate with an implant for anchoring suture.

DETAILED DESCRIPTION OF THE INVENTION

Figure 1:
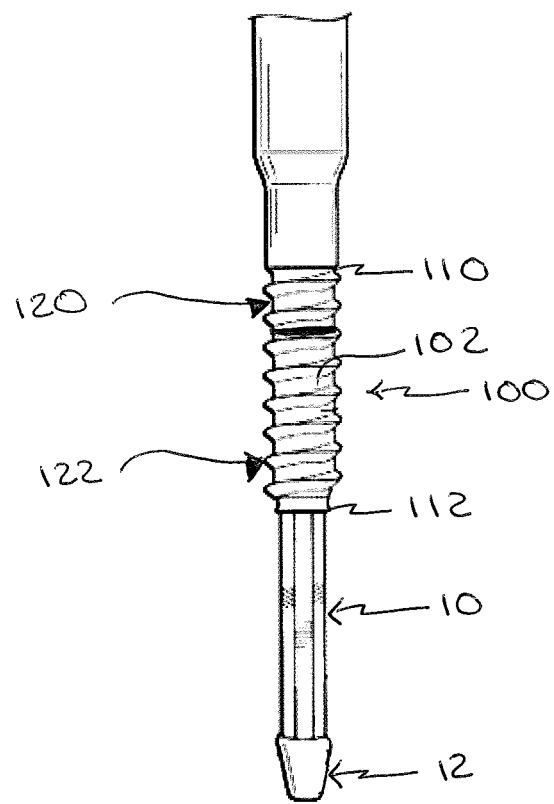
FIG. 1 is a perspective view of a suture anchor according to an exemplary embodiment of the present invention, showing the suture anchor used with two different types implants.
Figure 2:
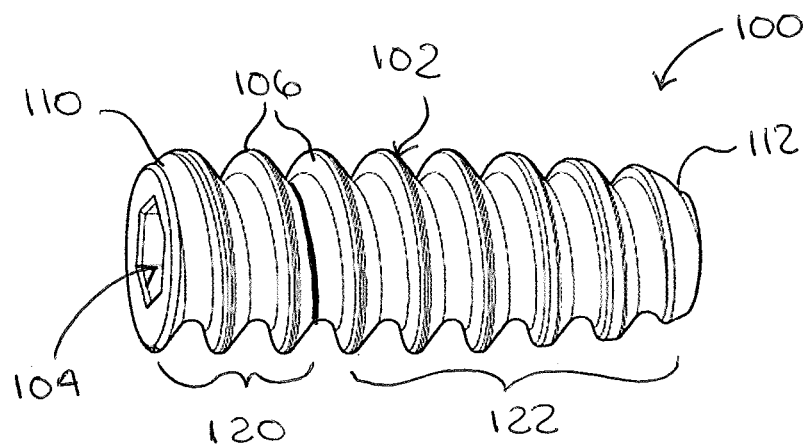
FIG. 2 is a perspective view of the suture anchor illustrated in FIG. 1.

Referring to the figures, the present invention generally relates to a suture anchor 100 that may have a portion formed of human cortical bone to maximize purchase with a bone hole and pull-out strength. FIG. 1 illustrates the suture anchor 100 in accordance with an exemplary embodiment of the present invention, received on a driver or inserter device 10 which has a cooperating implant 12 for insertion into a bone hole 90 (FIG. 4) for suture anchoring.

The suture anchor 100 generally includes a cannulated anchor body 102 with an inner bore 104 for receiving the inserter device 10 and outer bone gripping members, such as threads 106, similar, in a preferred embodiment, to the suture anchor disclosed in commonly owned U.S. Pat. No. 8,663, 279, the subject matter of which is herein incorporated by reference. However, the present invention can be incorporated in any suture anchor.

Figure 3A:
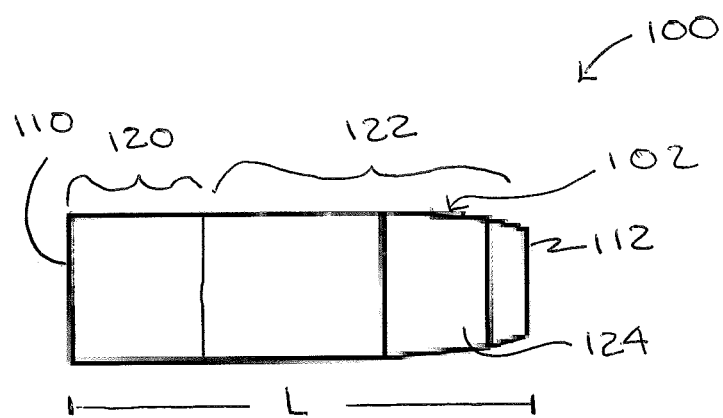
FIG. 3A is a side elevation view of the suture anchor illustrated in FIG. 1.
Figure 3B:
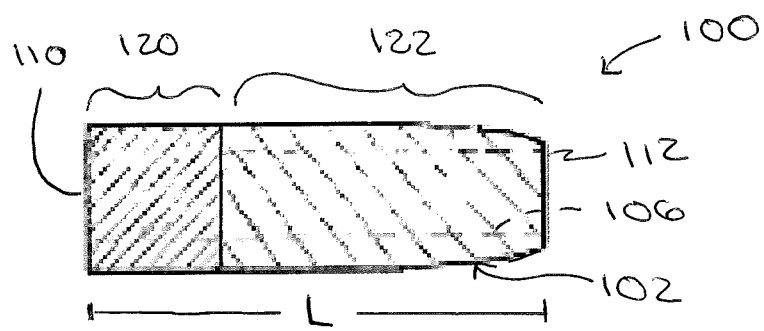
FIG. 3B is a side cross-sectional view of the suture anchor illustrated in FIG. 3A.

The anchor body 102 has a proximal end 110 that is configured to interface with the inserter device 10 (FIGS. 1 and 4) and an opposite distal end 112, which is the end of the anchor 100 that is first inserted into the bone hole 90 (FIG. 4) for installation of anchor 100. The anchor body 102 has an insertion length L defined between the proximal and distal ends 110 and 112, as seen in FIG. 3A. The anchor body 102 preferably has two sections, a proximal section 120 and a main section 122 where the sections 120 and 122 are forming of different materials from one another, as seen in FIG. 3B.

The proximal section 120 is remote from the distal end 112 of the anchor body 102 and ends at the proximal end 110. The main section 122 ends at the distal end 112. In a preferred embodiment, the proximal section 120 makes up no more than about one-third of the anchor body 102, that is the length of the proximal section 120 is no more than about one-third of the body's insertion length L. The proximal section 120 is formed of a biologic material, such as human cortical bone, to facilitate boney integration of the anchor when inserted in the bone hole and to provide an increased contact area for the footprint to heal the injury. In a preferred embodiment, only the proximal section 120 is formed of human cortical bone.

The main section 122 may be formed of any biocompatible material other than human cortical bone, such as a bioabsorbable material, a biocomposite composite material, PLLA and nonabsorbable PEEK or titanium materials. The major diameter of the main section 122 of the anchor body 102 may be generally constant but can have a tapered portion 124 that generally taper inwardly to a narrow end at the distal end 112 of the anchor body 102, as best seen in FIGS. 3A and 3B, to facilitate insertion into the bone hole 90. Bone hole 90 may be pre-drilled and pre-tapped to receive the anchor 100. Alternatively, the anchor 100, particularly the distal end 112 and the main section 122 may be self-punching and/or self-tapping. Because the anchor body 102 is generally cylindrical, the inserter 10 holds the proximal section 120 and main section of the anchor body 102 together, such that they abut against each other with their thread pitches lined up, so that both sections 120 and 122 may be driven into the bone hole adjacent to each other.

Figure 4:
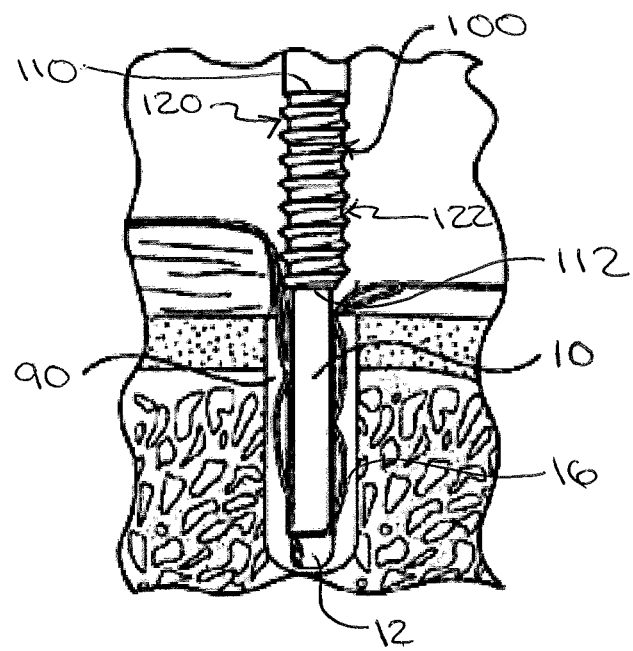
FIG. 4 is a view of the suture anchor illustrated in FIG. 1, showing the suture anchor being inserted into a bone hole.
Figure 5:
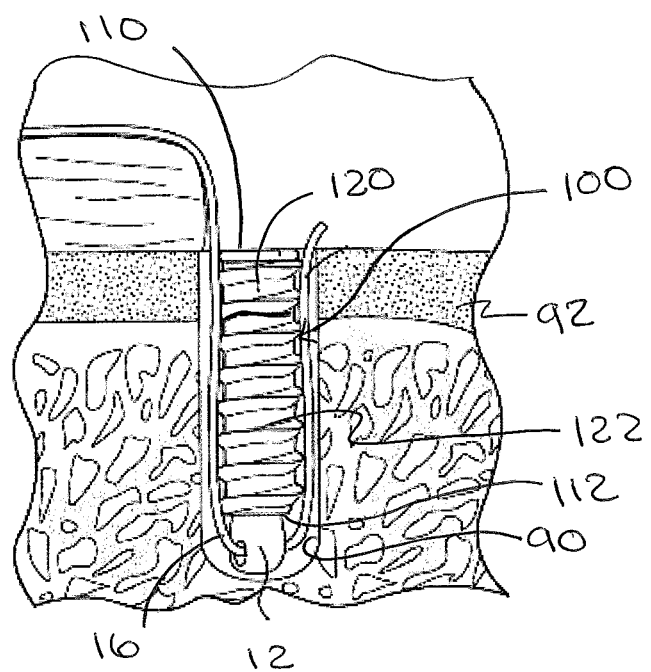
FIG. 5 is a view of the suture anchor similar to FIG. 4, showing the suture anchor installed into the bone hole.

As seen in FIGS. 4 and 5, the anchor 100, and specifically the distal end 112 of the anchor body 102, cooperates with the implant 12 for anchoring sutures 16 in the bone hole 90 in a manner similar to that described in U.S. Pat. No. 8,663,279. As seen in FIG. 4, the implant 12 (supporting sutures 16) is first installed into the bone hole 90 using the inserter 10. The suture anchor 100 may then be driven into the bone hole 90 by the inserter 10 and/or its associated driver until the distal end 112 of the anchor body 102 interfaces with the implant 12, as seen in FIG. 5. In doing so, the inserter 10 holds the proximal and main sections 120 and 122 of the anchor body 102, such that they abut against each other with their thread pitches lined up, so that both sections 120 and 122 may be driven into the bone hole adjacent to each other. The proximal section 120 of the anchor body 102 engages the humeral cortical bone layer 92 of the bone hole 90. Because the proximal section 120 of the anchor is formed of a biologic material such as human cortical bone, the engagement between the anchor 100 and the bone hole 90 is improved due to the boney integration between the cortical bone layer 92 and the proximal section 120 of the anchor. Biologic material such as cortical bone can advantageously wick the patient's bone marrow elements and can also be soaked as a biologic delivery device. The features and advantages in turn improve the pull-out strength of the anchor 100.

It should be understood that terms such as "lateral," "medial," "distal," "proximal," "superior," and "inferior" are used above consistent with the way those terms are used in the art. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content

What is claimed is:

1. A suture anchor for tissue repair, comprising:
   a cannulated anchor body having proximal and distal ends, and an insertion length defined therebetween, the cannulated anchor body comprising a proximal section and a main section, the proximal section being remote from the distal end and ending at the proximal end of the cannulated anchor body and the main section ending at the distal end of the cannulated anchor body, and the proximal section being no more than about one-third of the insertion length of the cannulated anchor body,
   wherein the proximal and main sections are formed of different materials, and only the proximal section is formed of a biologic material.

2. The suture anchor of claim 1, wherein the proximal section is formed of human cortical bone.

3. The suture anchor of claim 1, wherein the main section is formed of a biocompatible material.

4. The suture anchor of claim 1, wherein the main section includes an inwardly tapered portion near the distal end.

5. The suture anchor of claim 1, wherein the cannulated anchor body has outwardly extending threads.

6. The suture anchor of claim 1, wherein the cannulated anchor body includes an inner bore adapted to receive an inserter.

7. A suture anchor for tissue repair, comprising:
   a cannulated anchor body having proximal and distal ends, and an insertion length defined therebetween, the proximal end being configured to interface with an inserter and the distal end being configured to cooperate with an implant for suture anchoring, the cannulated anchor body comprising a proximal section and a main section, the proximal section being remote from the distal end of the cannulated anchor body and ending at the proximal end and the main section ending at the distal end of the cannulated anchor body, the main section having an inwardly tapered portion at the distal end, and the proximal section being no more than about one-third of the insertion length of the cannulated anchor body,
   wherein the proximal and main sections are formed of different materials, and only the proximal section is formed of a biologic material.

8. The suture anchor of claim 7, wherein the proximal section is formed of human cortical bone.

9. The suture anchor of claim 7, wherein the main section is formed of a biocompatible material.

10. The suture anchor of claim 9, wherein the main section is formed of bioabsorbable material, a biocomposite composite material, PLLA, or nonabsorbable PEEK.

11. The suture anchor of claim 7, wherein the cannulated anchor body has outwardly extending threads.

12. A suture anchor and inserter for tissue repair, comprising:
    a suture anchor comprising:
       a cannulated anchor body having a proximal end and a distal end, and an insertion length defined therebetween, the proximal end being configured to interface with an inserter and the distal end being configured to cooperate with an implant for suture anchoring, the cannulated anchor body comprising a proximal section and a main section, the proximal section ending at the proximal end remote from the distal end and the main section ending at the distal end, the proximal section having a length that is about one-third of the insertion length of the cannulated anchor body,
    wherein the proximal and main sections being formed of different materials, and only the proximal section is formed of a biologic material, and wherein each of the proximal and main sections has threads with a thread pitch; and
    an inserter for inserting the suture anchor into bone, the inserter holding the proximal section and the main sections together such that they abut against each other with their thread pitches lined up, whereby the proximal section and the main section are driven into the bone hole adjacent to each other.

13. The suture anchor and inserter of claim 12, wherein the main section is formed of a biocompatible material.

14. The suture anchor and inserter of claim 12, wherein the proximal section is formed of human cortical bone.

15. The suture anchor and inserter of claim 12, wherein the main section includes an inwardly tapered portion near the distal end.

16. The suture anchor and inserter of claim 12, wherein the threads of each of the proximal and main sections are outwardly extending threads.

17. The suture anchor and inserter of claim 12, wherein the distal end and/or the main section of the suture anchor is self-punching and/or self-tapping to facilitate insertion of the anchor.

* * * * *